United States Patent
Marcotte

(10) Patent No.: US 6,420,369 B1
(45) Date of Patent: Jul. 16, 2002

(54) ANTICONVULSANT DERIVATIVES USEFUL IN TREATING DEMENTIA

(75) Inventor: David B. Marcotte, Charlotte, NC (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/571,607

(22) Filed: May 15, 2000

Related U.S. Application Data

(60) Provisional application No. 60/135,454, filed on May 24, 1999.

(51) Int. Cl.$^7$ .................... A61K 31/505; A61K 31/35; A61K 31/18
(52) U.S. Cl. .................. 514/258; 514/454; 514/455; 514/456; 514/459; 514/601
(58) Field of Search ................. 514/454, 455, 514/456, 459, 601, 258

(56) References Cited

U.S. PATENT DOCUMENTS

| | | | |
|---|---|---|---|
| 4,513,006 A | 4/1985 | Maryanoff et al. | 514/23 |
| 5,387,700 A | 2/1995 | Maryanoff et al. | 514/387 |
| 5,753,693 A | 5/1998 | Shank | 514/454 |

FOREIGN PATENT DOCUMENTS

| WO | WO 00/32183 | 6/2000 |
|---|---|---|

OTHER PUBLICATIONS

Shank, R. et al "Topiramate: preclinical evaluation of a structurally novel anticonvulsant" Epilepsia, vol. 35, No. 2, pp. 450–460, 1994.*
Hermann, N. et al "Behavioural disorders in demented elderly patients" CNS Drugs, vol. 6, no 4, pp. 280–300, 1996.*
Physicians' Desk Reference, 49th edition, pp. 1193–1196, 1995.*
Merck Manual Online [http://www.merck.com/pubs/mmanual/section15/chapter189/189d.htm] accessed Sep. 2001.*
William M. Regan et al., "Abapentin for Behavioral Agitation in Alzheimer's Disease", J. Clin, Psycholpharmacol, vol. 17, No.1, Feb. 1997.
LJ Sheldon et al., "Gabapentin in Geriatric Psychiatry Patients", The Canadian Journal of Psychiatry, vol. 43, No. 4, May 1998.
Carolyn M. Mazure et al., "Valproate Treatment of Older Psychotic Patients with Organic Mental Syndromes and Behavorial Dyscontorl", The American Geriatrics Society, 40:914–916 1992.

Pierre N. Tariot et al., "Efficacy and Tolerability of Carbamazepine for Agitation and Aggression in Dementai", Am. J. Psychiatry, 155:1, Jan. 1998, p. 54–61.
Pierre N. Tariot et al., "Lack of Carbamazepine Toxicity in Frail Nursing Home Patients: A Controlled Study", American Geriatrics Society, 43:1026–1029, 1995.
Carlo Dallocchio et al., "Combination of Donepezil and Gabapentin for Behavorial Disorders in Alzheimer's Disease", J. Clin Psychiatry 61;Jan. 1, 2000.
Marcotte DB. Use of the new antiiepileptic drug topiramate as a mood stabilizer. In: Syllabus and proceedings summary of the annual meeating of the American Psychiatric Association; May 30–Jun. 4, 1998; Toronto, Ontario, Canada. Abstract 115.
David Marcotte, "Use of topiramate, a new anti–epileptic as a mood stabilizer", Journal of Affective Disorders, 50 (1998) 245–251.
Murray A. Raskind, "Evaluation and Management of Aggressive Behavior in the Elderly Demented Patient", J. Clin Psychiatry 1999;60 45–49.
William D. Sandborn, et al., "Valporic Acid for Physically Agrressive Behavior in Geriatric Patients", The American Journal of Geriatric Psychiatry, 1995;3:239–242.
Colm Cooney et al., "Carbamazepine Use in agrressive Behavior Associated with Senile Dementia", International Journal of Geriatric Psychiatric, vol. 11: 901–905 (1996).
Alan M. Mellow et al., "Sodium Valproate in the Treatment of Behavioral Disturbance in Dementia", Journal of geriatric Psychiatry and Neurology, vol. 6, Oct.–Dec. 1993 p. 205–209.
David M. Roane et al., "Treatment of Dementia Associated Agitation with Gabapentin", J. Neuropsychiatry Clin Neurosci 12:1, Winter 2000, p. 40–43.
Nathan Herrmann et al., "Valproic Acid Treatment of Agitation in Dementia", Can J Psychiatry vol. 43, Feb. 1998, p. 69–72.
Nathan Herrmann et al., Effectiveness of Gabapentin for the Treatment of Behavioral Disorders in Dementia, Journal of Clinical Psychopharmacology, vol. 20, No. 1, p. 90–93, 2000.

* cited by examiner

Primary Examiner—Kathleen K. Fonda
Assistant Examiner—Leigh C. Maier
(74) Attorney, Agent, or Firm—Mary Appollina

(57) ABSTRACT

Anticonvulsant derivatives useful in treating dementia and/or behavioral and psychotic disturbances in dementia are disclosed.

12 Claims, No Drawings

ANTICONVULSANT DERIVATIVES USEFUL IN TREATING DEMENTIA

CROSS-REFERENCE TO RELATED APPLICATION

This application claims priority from U.S. Ser. No. 60/135,454, filed May 24, 1999, the contents of which are hereby incorporated by reference.

BACKGROUND OF THE INVENTION

Compounds of Formula I:

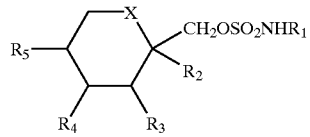

are structurally novel antiepileptic compounds that are highly effective anticonvulsants in animal tests (Maryanoff, B. E, Nortey, S. O., Gardocki, J. F., Shank, R. P. and Dodgson, S. P. *J. Med. Chem.* 30, 880–887, 1987; Maryanoff, B. E., Costanzo, M. J., Shank, R. P., Schupsky, J. J., Ortegon, M. E., and Vaught J. L. Bioorganic & Medicinal Chemistry Letters 3, 2653–2656, 1993). These compounds are covered by U.S. Pat. No. 4,513,006. One of these compounds 2,3:4,5-bis-O-(1-methylethylidene)-β-D-fructopyranose sulfamate known as topiramate has been demonstrated in clinical trials of human epilepsy to be effective as adjunctive therapy or as monotherapy in treating simple and complex partial seizures and secondarily generalized seizures (E. FAUGHT, B. J. WILDER, R. E. RAMSEY, R. A. REIFE, L D. KRAMER, G. W. PLEDGER, R. M. KARIM et. al., Epilepsia 36 (S4) 33, 1995; S. K. SACHDEO, R. C. SACHDEO, R. A. REIFE, P. LIM and G. PLEDGER, Epilepsia 36 (S4) 33, 1995), and is currently marketed for the treatment of simple and complex partial seizure epilepsy with or without secondary generalized seizures in approximately twenty countries including the United States, and applications for regulatory approval are presently pending in several additional countries throughout the world.

Compounds of Formula I were initially found to possess anticonvulsant activity in the traditional maximal electroshock seizure (MES) test in mice (SHANK, R. P., GARDOCKI, J. F., VAUGHT, J. L., DAVIS, C. B., SCHUPSKY, J. J., RAFFA, R. B., DODGSON, S. J., NORTEY, S. O., and MARYANOFF, B. E., Epilepsia 35 450–460, 1994). Subsequent studies revealed that Compounds of Formula I were also highly effective in the MES test in rats. More recently topiramate was found to effectively block seizures in several rodent models of epilepsy (J. NAKAMURA, S. TAMURA, T. KANDA, A. ISHII, K. ISHIHARA, T. SERIKAWA, J. YAMADA, and M. SASA, Eur. J. Pharmacol. 254 83–89, 1994), and in an animal model of kindled epilepsy (A. WAUQUIER and S. ZHOU, Epilepsy Res. 24, 73–77, 1996).

Dementia is a mental disorder characterized by general impairment of intellectual functioning including memory, orientation, perception, language, alteration in mood and affect and impairment of judgment and abstraction. There may be marked change in personality and behavior.

Dementia is diagnosed according to its etiology, the two most common (among multiple etiologies) being: Alzheimer's dementia and Vascular dementia. Alzheimer's dementia, which accounts for 50–60% of dementias, is a progressive dementia in which all known reversible causes have been ruled out. Vascular dementia is dementia of cerebrovascular origin which progresses in a stepwise fashion. Dementia is generally progressive and irreversible unless the etiology is treatable (10%).

The clinical course of dementia may show "primary" or cognitive symptoms as well as "secondary or behavioral symptoms." That is, patients with dementia (DSM IV) often exhibit troublesome and disruptive behaviors and symptoms of psychosis in addition to the cognitive impairments, presenting difficult management problems for both caregivers and healthcare providers. These include aggressive, non aggressive and verbally agitated behaviors (Cohen-Mansfield J. Marx M S. Rosenthal A S. Dementia and agitation in nursing home residents: how are they related? Psychology and aging. 5(1): 3–8,1990 March). Partial pharmacologic management of these behaviors include antipsychotics, benzodiazepines, beta-blockers, SSRI antidepressants and anticonvulsants (Yudofsky S C. Silver J M. Hales R E. Pharmacologic management of aggression in the elderly. Journal of Clinical Psychiatry. 51 Suppl: 22–8; discussion 29–32, 1990 October).

Both carbamazepine (Tariot P N, Erb R, Podgorski C A. Cox C. Patel S. Jakimovich L. Irvine C. Efficacy and tolerability of carbamazepine for agitation and aggression in dementia. American Journal of Psychiatry. 155(1): 54–61, 1998 January) and divalproex sodium (Kasckow, John W.; Mcelroy, Susan L.; Cameron, Renee L.; Mahler Leslie L.; Fudala Stanley J.; Curr. Ther. Res. (1997), 58(12), 981–989) have been shown to be efficacious in controlling behavioral agitation in some patients with dementia. Thus based on it's wider mode of action and in particular upon its GABA enhancing activity and the kainate/AMPA receptor inhibition of topiramate, we propose topiramate will be effective in the treatment of agitation and aggression in dementia. Indeed, this was the case in patients with dementia treated with the drug.

It is therefore an object of the invention to identify a method of treating dementia in a patient in need thereof. Still another object of the invention is to identify a method of treating behavioral and psychotic disturbances in dementia in a patient in need thereof.

DISCLOSURE OF THE INVENTION

Accordingly, it has been found that compounds of the following formula I:

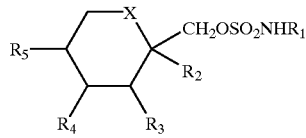

wherein X is O or $CH_2$, and R1, R2, R3, R4 and R5 are as defined hereinafter are useful in treating dementia and/or behavioral and psychotic disturbances in dementia.

DETAILED DESCRIPTION OF THE PREFERRED EMBODIMENTS

The sulfamates of the invention are of the following formula (I):

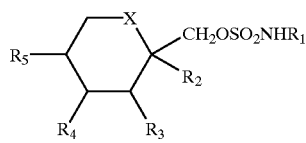

wherein
  X is $CH_2$ or oxygen;
  $R_1$ is hydrogen or $C_1$–$C_4$ alkyl; and
  $R_2$, $R_3$, $R_4$ and $R_5$ are independently hydrogen or $C_1$–$C_3$ alkyl and, when X is $CH_2$, $R_4$ and $R_5$ may be alkene groups joined to form a benzene ring and, when X is oxygen, $R_2$ and $R_3$ and/or $R_4$ and $R_5$ together may be a methylenedioxy group of the following formula (II):

wherein $R_6$ and $R_7$ are the same or different and are hydrogen, $C_1$–$C_3$ alkyl or are alkyl and are joined to form a cyclopentyl or cyclohexyl ring.

$R_1$ in particular is hydrogen or alkyl of about 1 to 4 carbons, such as methyl, ethyl, iso-propyl, n-propyl, n-butyl, isobutyl, sec-butyl and t-butyl. Alkyl throughout this specification includes straight and branched chain alkyl. Alkyl groups for $R_2$, $R_3$, $R_4$, $R_5$, $R_6$ and $R_7$ are of about 1 to 3 carbons and include methyl, ethyl, iso-propyl and n-propyl. When X is $CH_2$, $R_4$ and $R_5$ may combine to form a benzene ring fused to the 6-membered X-containing ring, i.e., $R_4$ and $R_5$ are defined by the alkatrienyl group =C—CH=CH—CH=.

A particular group of compounds of formula (I) is that wherein X is oxygen and both $R_2$ and $R_3$ and $R_4$ and $R_5$ together are methylenedioxy groups of the formula (II), wherein $R_6$ and $R_7$ are both hydrogen both alkyl or combine to form a spiro cyclopentyl or cyclohexyl ring, in particular where $R_6$ and $R_7$ are both alkyl such as methyl. A second group of compounds is that wherein X is $CH_2$ and $R_4$ and $R_5$ are joined to form a benzene ring. A third group of compounds of formula (I) is that wherein both $R_2$ and $R_3$ are hydrogen.

A particularly preferred compound for use in the methods of the present invention is 2,3:4,5-bis-O-(1-methylethylidene)-β-D-fructopyranose sulfamate, known as topiramate. Topiramate has the following structural formula

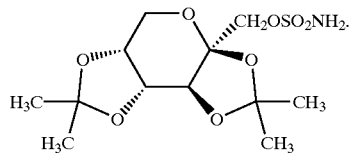

The compounds of formula (I) may be synthesized by the following methods:

(a) Reaction of an alcohol of the formula $RCH_2OH$ with a chlorosulfamate of the formula $ClSO_2NH_2$ or $ClSO_2NHR_1$ in the presence of a base such as potassium t-butoxide or sodium hydride at a temperature of about −20° to 25° C. and in a solvent such as toluene, THF or dimethylformamide wherein R is a moiety of the following formula (III):

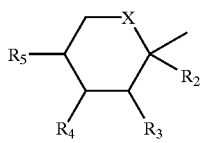

(b) Reaction of an alcohol of the formula $RCH_2OH$ with sulfurylchloride of the formula $SO_2Cl_2$ in the presence of a base such as triethylamine or pyridine at a temperature of about −40° to 25° C. in a solvent such as diethyl ether or methylene chloride to produce a chlorosulfate of the formula $RCH_2OSO_2Cl$.

The chlorosulfate of the formula $RCH_2OSO_2Cl$ may then be reacted with an amine of the formula $R_1NH_2$ at a temperature of abut 40° to 25° C. in a solvent such as methylene chloride or acetonitrile to produce a compound of formula (I). The reaction conditions for (b) are also described by T. Tsuchiya et al. in Tet. Letters, No. 36, p. 3365 to 3368 (1978).

(c) Reaction of the chlorosulfate $RCH_2OSO_2Cl$ with a metal azide such as sodium azide in a solvent such as methylene chloride or acetonitrile yields an azidosulfate of the formula $RCH_2OSO_2N_3$ as described by M. Hedayatullah in Tet. Lett. p. 2455–2458 (1975). The azidosulfate is then reduced to a compound of formula (I) wherein $R_1$ is hydrogen by catalytic hydrogenation, e.g. with a noble metal and $H_2$ or by heating with copper metal in a solvent such as methanol.

The starting materials of the formula $RCH_2OH$ may be obtained commercially or as known in the art. For example, starting materials of the formula $RCH_2OH$ wherein both $R_2$ and $R_3$ and $R_4$ and $R_5$ are identical and are of the formula (II) may be obtained by the method of R. F. Brady in Carbohydrate Research, Vol. 14, p. 35 to 40 (1970) or by reaction of the trimethylsilyl enol ether of a $R_6COR_7$ ketone or aldehyde with fructose at a temperature of about 25° C., in a solvent such as halocarbon, e.g. methylene chloride in the presence of a protic acid such as hydrochloric acid or a Lewis Acid such as zinc chloride. The trimethylsilyl enol ether reaction is described by G. L. Larson et al in J. Org. Chem. Volaa 38, No. 22, p. 3935 (1973).

Further, carboxylic acids and aldehydes of the formulae RCOOH and RCHO may be reduced to compounds of the formula RCH2OH by standard reduction techniques, e.g. reaction with lithium aluminum hydride, sodium borohydride or borane-THF complex in an inert solvent such as diglyme, THF or toluene at a temperature of about 0° to 100° C., e.g. as described by H. O. House in "Modem Synthetic Reactions", 2nd Ed., pages 45 to 144 (1972).

The compounds of formula I: may also be made by the processes disclosed in U.S. Pat. Nos. 4,513,006 and 5,387,700, all of which are incorporated herein by reference. More particularly, topiramate may be prepared following the process described in Examples 1 to 3 of U.S. Pat. No. 5,387,700.

The compounds of formula I include the various individual isomers as well as the racemates thereof, e.g., the various alpha and beta attachments, i.e., below and above the plane of the drawing, of $R_2$, $R_3$, $R_4$ and $R_5$ on the 6-membered ring. Preferably, the oxygen of the methylenedioxy group (II) are attached on the same side of the 6-membered ring.

The term "subject" as used herein, refers to an animal, preferably a mammal, most preferably a human, who has been the object of treatment, observation or experiment.

The term "dementia" as used herein, refers to the primary or cognitive symptoms of dementia characterized by general impairment of intellectual functioning, and includes but is not limited to the conditions of Alzheimer's dementia and vascular dementia.

The term "behavioral and psychotic disturbances in dementia" as used herein, refers to the secondary symptoms associated with dementia. Examples of behavioral and psychotic disturbances in dementia include, but are not limited to, impairment of self care (dressing, eating, bathing), agitation including motor restlessness, verbal and physical aggression, sleep disruption, wandering and incontinence, repetitive behaviors, disinhibition, including inappropriate sexual behaviors, "sundowning" characterized by agitation, restlessness, panic, intensified disorientation and verbal or physical outbursts in the afternoon or evening, and psychotic symptoms (e.g., delusions, hallucinations, paranoia).

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

For treating dementia and/or behavioral and psychotic disturbances in dementia, a compound of formula (I) may be employed at a total daily dosage in the range of about 15 mg to about 500 mg, preferably, about 15 mg to about 400 mg, for an average adult human, administered one to four times per day, preferably, one to two times per day. A unit dose typically contains about 16 mg to about 300 mg, preferably, about 16 mg to about 200 mg, of the active ingredient.

Additionally, a non-typical antipsychotic such as Riperdale® (risperidone) may be administered along with the anticonvulsants of formula (I) of the present invention for treating dementia and/or behavioral and psychotic disturbances in dementia. In accordance with the methods of treatment of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Optimal dosages to be administered may be readily determined by those skilled in the art, and will vary with the particular compound used, the mode of administration, the strength of the preparation, the mode of administration, and the advancement or severity of the disease condition. In addition, factors associated with the particular patient being treated, including patient age, weight, diet and time of administration, will result in the need to adjust dosages.

To prepare the pharmaceutical compositions of this invention, one or more sulfamate compounds of formula (I) are intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. For parenterals, the carrier will usually comprise sterile water, though other ingredients, for example, for purposes such as aiding solubility or for preservation, may be included. Injectable solutions may also be prepared in which case appropriate stabilizing agents may be employed. Topiramate is currently available for oral administration in round tablets containing 25 mg, 1 00 mg or 200 mg of active agent. The tablets contain the following inactive ingredients: lactose hydrous, pregelatinized starch, microcrystalline cellulose, sodium starch glycolate, magnesium stearate, purified water, carnauba wax, hydroxypropyl methylcellulose, titanium dioxide, polyethylene glycol, synthetic iron oxide, and polysorbate 80.

The pharmaceutical compositions herein will contain, per dosage unit, e.g., tablet, capsule, powder, injection, teaspoonful, suppository and the like from about 25 to about 200 mg of the active ingredient.

The following Examples are set forth to aid in the understanding of the invention, and are not intended and should not be construed to limit in any way the invention set forth in the claims which follow thereafter.

A retrospective analysis of patients treated in an open label manner with topiramate for dementia and/or behavioral and psychotic disturbances in dementia was performed.

EXAMPLE 1

The charts of 58 consecutive patients with diagnosed psychiatric disorders refractory to conventional mood stabilizers who were treated with topiramate were selected for retrospective review. Topiramate 25 mg BID was added to existing pharmacotherapy on an open label basis. It was titrated upward in 50 mg (25 mg bid) increments every seven days until improvement occurred or a total dosage of 400 mg per day was reached. Charts were retrospectively reviewed for the following data: demographic information, psychiatric diagnosis and duration of illness, general medical history, daily dose of topiramate and regimen, duration of topiramate therapy, reason for discontinuation of topiramate therapy, previous therapy, concurrent medications, adverse events and evaluation of response to topiramate.

Results were analyzed using descriptive statistics. When possible, results are expressed as means with standard deviation (SD). Response was rated on a Likert scale from "worse", to "no change", to "minimally improved", to "markedly improved". Improvement was investigator rated and included a qualitative assessment of changes in sleep, appetite, mood and concentration during therapy. Adverse events reported by the patients were recorded during therapy and assessed for their relationship to study therapy.

Of the 58 patients, three had dementia and two had psychosis, not otherwise specified; all of the subjects with dementia or psychosis were inpatients. For the dementia patients, the daily mean dose of topiramate was 210 mg and the duration of treatment was 11.7 weeks. For the psychotic patients, the daily mean dose of topiramate was 260 mg and the duration of treatment was 10.7 weeks. Several of the patients were taking Risperdal® (risperidone) as concurrent psychiatric medication. All three patients with dementia and both patients with psychosis had marked or moderate improvement while on topiramate.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method for treating dementia in a subject in need thereof comprising administering to the subject a therapeutically effective amount of a compound of the formula I:

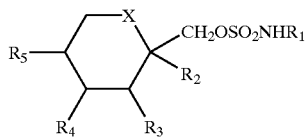

wherein
- X is $CH_2$ or oxygen;
- $R_1$ is hydrogen or $C_1$–$C_4$ alkyl; and
- $R_2$, $R_3$, $R_4$ and $R_5$ are independently hydrogen or $C_1$–$C_3$ alkyl and, when X is $CH_2$, $R_4$ and $R_5$ may be alkene groups joined to form a benzene ring and, when X is oxygen, $R_2$ and $R_3$ and/or $R_4$ and $R_5$ together may be a methylenedioxy group of the following formula (II):

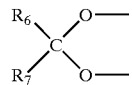

wherein $R_6$ and $R_7$ are the same or different and are hydrogen, $C_1$–$C_3$ alkyl or $R_6$ and $R_7$ together with the carbon to which they are attached are joined to form a cyclopentyl or cyclohexyl ring.

2. The method of claim 1, wherein the compound of formula I is topiramate.

3. The method of claim 1, wherein the therapeutically effective amount is from about 15 mg to about 500 mg per day.

4. The method of claim 1, wherein the therapeutically effective amount is from about 15 mg to about 400 mg per day.

5. The method of claim 1, wherein the compound is administered as a pharmaceutical composition.

6. The method of claim 1 wherein the compound is administered in combination with an antipsychotic agent which is risperidone.

7. A method of treating behavioral and psychotic disturbances in dementia in a subject in a subject in need thereof comprising administering to the subject a therapeutically effective amount of a compound of the formula I:

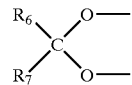

wherein
- X is $CH_2$ or oxygen;
- $R_1$ is hydrogen or $C_1$–$C_4$ alkyl; and
- $R_2$, $R_3$, $R_4$ and $R_5$ are independently hydrogen or $C_1$–$C_3$ alkyl and, when X is $CH_2$, $R_4$ and $R_5$ may be alkene groups joined to form a benzene ring and, when X is oxygen, $R_2$ and $R_3$ and/or $R_4$ and $R_5$ together may be a methylenedioxy group of the following formula (II):

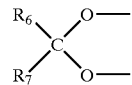

wherein $R_6$ and $R_7$ are the same or different and are hydrogen, $C_1$–$C_3$ alkyl or $R_6$ and $R_7$ together with the carbon to which they are attached are joined to form a cyclopentyl or cyclohexyl ring.

8. The method of claim 7, wherein the compound of formula I is topiramate.

9. The method of claim 7, wherein the therapeutically effective amount is from about 15 mg to about 500 mg per day.

10. The method of claim 7, wherein the therapeutically effective amount is from about 15 mg to about 400 mg per day.

11. The method of claim 7, wherein the compound is administered as a pharmaceutical composition.

12. The method of claim 7 wherein the compound is administered in combination with an antipsychotic agent which is risperidone.

* * * * *

UNITED STATES PATENT AND TRADEMARK OFFICE
CERTIFICATE OF CORRECTION

PATENT NO. : 6,420,369 B1
DATED : July 16, 2002
INVENTOR(S) : David B. Marcotte

It is certified that error appears in the above-identified patent and that said Letters Patent is hereby corrected as shown below:

<u>Title page,</u>
Item [60], Related U.S. Application Data, should read:

-- [60]  Related U.S. Application Data
Provisional Application No. 60/136,454 filed on May 28, 1999 --

Signed and Sealed this

Twenty-ninth Day of April, 2003

JAMES E. ROGAN
*Director of the United States Patent and Trademark Office*